(12) United States Patent
Sabbagh

(10) Patent No.: US 6,978,786 B2
(45) Date of Patent: Dec. 27, 2005

(54) DEVICE FOR TREATING THE TEMPOROMANDIBULAR JOINT

(76) Inventor: Aladin Sabbagh, Stettiner Str. 19, 90424 Nuremberg (DE)

( * ) Notice: Subject to any disclaimer, the term of this patent is extended or adjusted under 35 U.S.C. 154(b) by 0 days.

(21) Appl. No.: 10/650,525

(22) Filed: Aug. 28, 2003

(65) Prior Publication Data

US 2004/0134499 A1    Jul. 15, 2004

(30) Foreign Application Priority Data

Aug. 28, 2002   (DE) ................................ 102 39 464

(51) Int. Cl.[7] ............................................. A61C 5/14
(52) U.S. Cl. ........................ 128/859; 433/6; 128/861
(58) Field of Search ................................ 128/859, 848, 128/861, 862; 602/902; 433/6

(56) References Cited

U.S. PATENT DOCUMENTS

| | | | |
|---|---|---|---|
| 3,488,848 A | | 1/1970 | Lerman |
| 4,211,008 A | | 7/1980 | Lerman |
| 4,573,916 A | * | 3/1986 | Sturtzkopf .................. 433/71 |
| 4,881,896 A | * | 11/1989 | Bergersen ..................... 433/5 |
| 4,919,668 A | * | 4/1990 | Rosenbaum et al. ..... 623/17.17 |
| 4,976,618 A | * | 12/1990 | Anderson ................... 433/215 |
| 5,368,477 A | * | 11/1994 | Neeley ........................ 433/6 |
| 5,837,004 A | * | 11/1998 | Lavore ...................... 607/109 |
| 6,164,278 A | * | 12/2000 | Nissani ..................... 128/848 |

FOREIGN PATENT DOCUMENTS

DE          3790568         8/1999

* cited by examiner

*Primary Examiner*—Henry Bennett
*Assistant Examiner*—Camtu Nguyen
(74) *Attorney, Agent, or Firm*—Fish & Richardson P.C., P.A.

(57) ABSTRACT

The invention relates to a device for treating the temporomandibular joint. The device includes pads (5) for placing on the occlusal surfaces of the posterior teeth (Z) of the left-hand and right-hand sides of the mouth, wherein the pads are filled with fluid (F), and are connected to each other by means of a tube (7) for fluid exchange. To improve the wearing comfort, it is proposed according to the invention that each pad (5) has on one side of it a means (1, 3, 4, 8) for clamping on the posterior tooth (Z).

15 Claims, 2 Drawing Sheets

DEVICE FOR TREATING THE TEMPOROMANDIBULAR JOINT

CROSS REFERENCE TO RELATED APPLICATIONS

This application claims priority under 35 U.S.C. §119(a) of German Application Number DE 102 39 464.4-23, filed Aug. 28, 2002.

TECHNICAL FIELD

This invention relates to the temporomandibular joint, and more particularly to methods and materials for treating dysfunctions of the temporomandibular joint.

BACKGROUND

Previous devices for treating dysfunctions of the temporomandibular joint are placed into the mouth in such a way that one pad lies on the occlusal surface of the posterior teeth of one side and another pad lies on the occlusal surface of the posterior teeth of the other side. A tube connecting the pads is positioned labially past the upper incisor teeth. Because of a fluid connection between the two pads, a hydrostatic pressure equalization takes place when biting together occurs; on the side on which a higher pressure is applied to the pads, fluid is displaced and forced into the other pad via the tube. The temporomandibular joints and muscles are then subjected to uniform loading. A dysfunction of the temporomandibular joint caused by one-sided loading of the temporomandibular joints and muscles can consequently be recognized and, if appropriate, treated with therapy.

For retaining the known devices in the upper jaw, a flexible tab extending bucally from each of the pads is provided. The tab lies against the gums. In practice, however, it has been found that this does not ensure adequate retention of the device. Particularly during speaking, the pads often lift off the posterior teeth and then have to be brought back again into the correct position. When the device is worn in the upper jaw, it is visible. As a consequence of this, patients do not like wearing it during the day, which is detrimental to successful therapy.

An object of the invention is to eliminate the disadvantages of the known devices. In particular, the invention provides a device for treating the temporomandibular joint which can be worn comfortably and unobtrusively.

SUMMARY

The invention provides a device for treating dysfunctions of the temporomandibular joint of the jaw. The devices of the invention include two pads. Each pad has on one side of it a means for clamping on the posterior tooth. Improved retention in the jaw is achieved in this way. The pads cannot come away from the posterior teeth. The device can be worn unobtrusively in the lower jaw, which facilitates continuous therapy.

In one aspect, the invention provides a device for treating a temporomandibular joint. A device of the invention includes first and second pads (5), wherein the first and second pads have a cavity, wherein the cavity is filled with fluid (F), wherein the first and second pads (5) are connected to each other by means of a tube (7), wherein the first and second pads (5) comprise means (1, 3, 4, 8) for clamping the pads (5) on a posterior tooth (Z).

In one embodiment, the first and second pads are formed by an envelope produced from a flexible material. In other embodiments, the means for clamping comprise at least one clip (8) or at least two clips (8) bent in a way that corresponds to the contour of the posterior tooth (Z). In another embodiment, the clip (8) can be cast into a clamping shoe (1), wherein the clamping shoe (1) is produced from plastic (e.g., transparent plastic). The clamping shoe (1) can be formed in a U profile with one or more legs (3, 4) extending from a base area (2). For example, the height (H) of the legs (3, 4) can correspond to the height of the posterior teeth (Z). In addition, the legs (3, 4) generally include a buccal leg (3) and/or a lingual leg (4). In another embodiment, the tube (7) can be fastened to the buccal leg (3) of the clamping shoe (1). For example, the tube (7) can be connected to a passage (6) extending through the buccal leg (3) to the pad (5), and the connection of the tube (7) to the passage (6) can be located at one end (E) of the buccal leg (3).

In one embodiment, the clamping shoe (1) is produced in an integral form with at least one of the pads (5). The clamping shoe (1) can be produced by thermoforming or by injection-molding. In an embodiment, the first and second pads can be positioned on the occlusal surfaces of the posterior teeth (Z) of the left-hand and right-hand sides of a mouth.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

The invention provides a device for treating dysfunctions of the temporomandibular joint of the jaw. The devices of the invention include two pads. Each pad has on one side of it a means for clamping on the posterior tooth. Improved retention in the jaw is achieved in this way. The pads cannot come away from the posterior teeth. The device can be worn unobtrusively in the lower jaw, which facilitates continuous therapy.

The means for clamping generally has at least one, preferably two, clips bent in a way corresponding to the contour of the posterior tooth. The clip can be produced from a stainless metal or from a rigid plastic. The clip is advantageously cast into a clamping shoe produced from plastic. This counteracts a risk of injury caused by the clips. The provision of a clamping shoe also contributes to improved retention of the device. The clamping shoe may be formed in the manner of a U profile with two legs extending from a base area. The legs are expediently bent slightly inward in a manner corresponding to the shape of the clips. The base area may be formed in such a way so as to correspond to the morphology of the occlusal surface of the posterior tooth. The clamping shoe rests in a largely form-fitting manner on the posterior teeth. This further contributes to improved retention. The height of the legs generally corresponds to the height of the posterior teeth, which avoids irritation of the gums.

Figure 1:
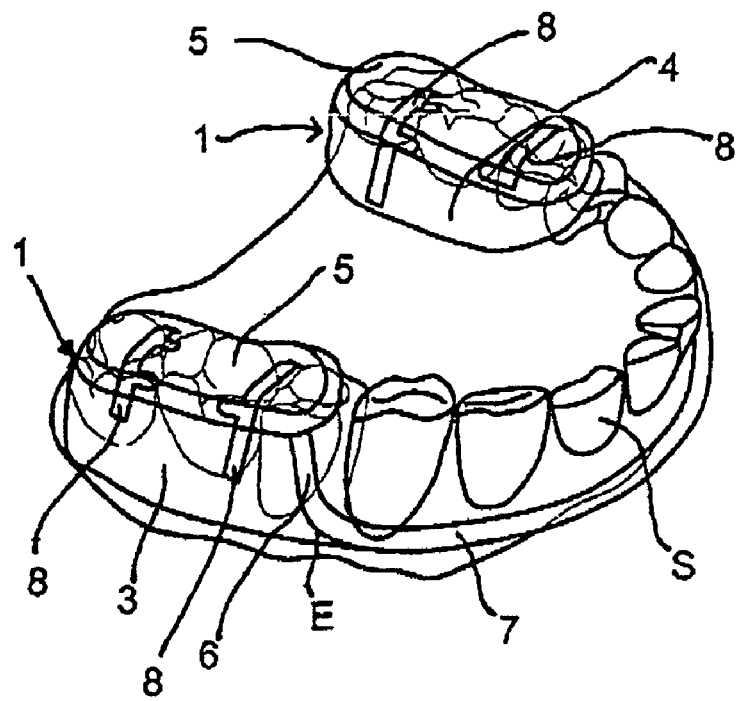
FIG. 1 shows a perspective view of a device of the invention accommodated in the jaw.
Figure 2:
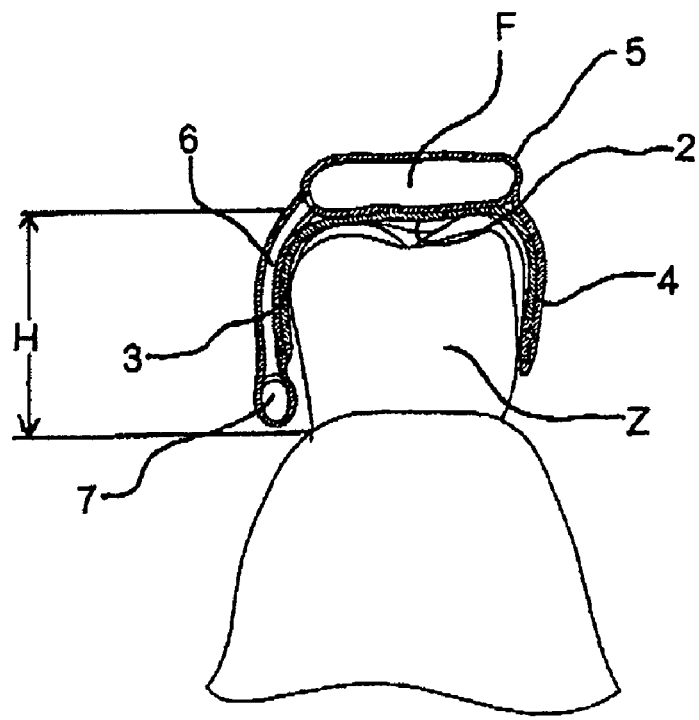
FIG. 2 shows a schematic sectional view through a clamping shoe according to FIG. 1.
Figure 3:
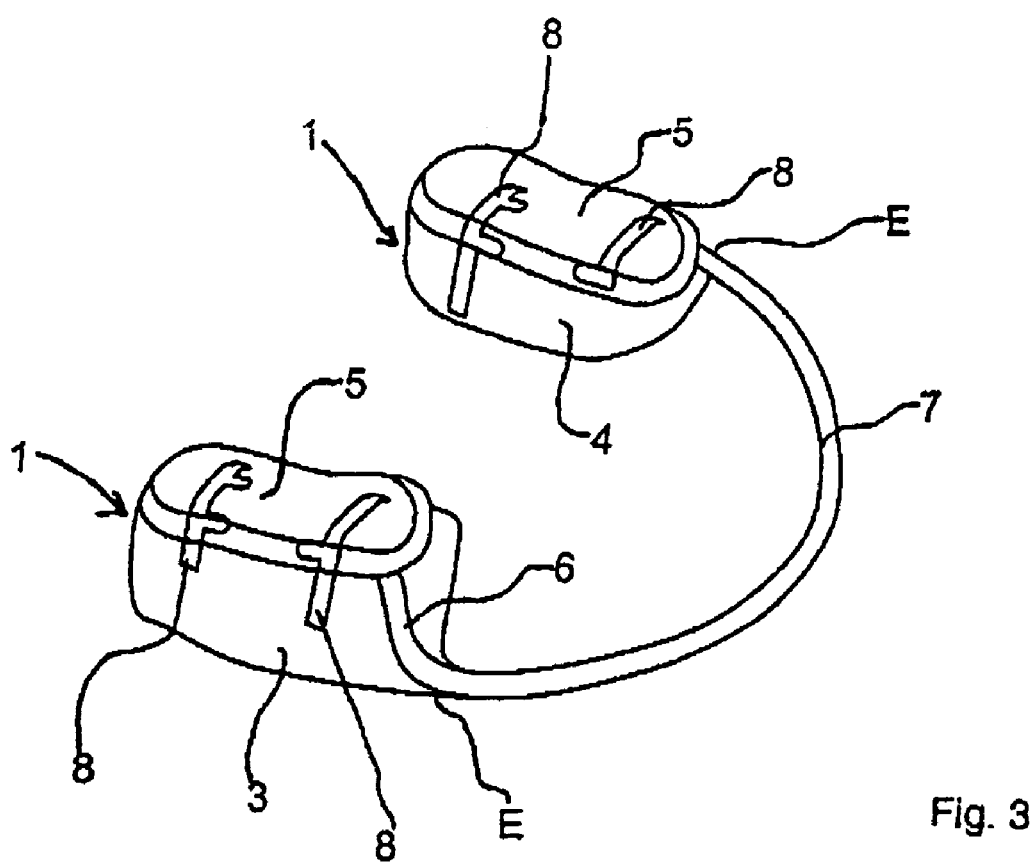
FIG. 3 shows a perspective view of a device of the invention.

The device shown in FIGS. 1–3 has two clamping shoes 1, 7 formed in a U profile. Each of the clamping shoes 1 comprises, in cross section, a base area 2 from which extends a buccal leg 3 facing the cheek and a lingual leg 4 facing the tongue. As can be seen in FIG. 2, the base area 2 and the legs 3, 4 are retained on the posterior tooth Z in a substantially form-fitting manner. On the side facing away from the occlusal surface of the posterior tooth Z, the clamping shoe 1 is connected to a pad 5. The pads 5 are filled with a fluid F. A passage 6 extending through the buccal leg 3 connects the pads 5 to the tube 7. The tube 7 is attached at the ends E of the buccal legs 3 facing the lips. When being worn, the tube 7 is taken labially past the incisor teeth S and connects the two pads 5 to each other for fluid equalization. The clamping shoes 1 are advantageously produced from a transparent plastic. To improve the clamping retention on the posterior teeth Z, clips 8 produced from metal may be advantageously cast into the clamping shoes 1. Two clips 8 are advantageously cast into each of the clamping shoes 1. The height H of the legs 3, 4 is generally less than the height of the posterior teeth Z. This avoids injury of the gums.

It goes without saying that the embodiment shown may be modified within the scope of the invention. For example, the clamping shoes 1 can be produced in an integral form with the pads 5. In addition, the clamping shoes 1 can be produced from a soft plastic. To ensure secure retention, the clamping shoes 1 can be provided with clips 8. It may also be that the tube 7 is produced in an integral form with the pads 5 and the clamping shoes 1.

According to one embodiment, a tube is respectively fastened to the buccal legs of a clamping shoe. The tube may be connected to a passage extending through the buccal leg to the pad. The connection of the tube to the passage or the fastening of the tube is located at the end of the buccal leg that faces the lips when the device is being worn.

According to another embodiment, the clamping shoe is produced in an integral form with the pad. The clamping shoe can be produced by thermoforming or injection molding. In this case, the pad can be fused or adhesively bonded to the clamping shoe at a subsequent time. In this case, each pad is connected over its full surface area to the respective clamping shoe. This avoids undesired deposits forming between the pad and the clamping shoe.

According to yet another embodiment, the plastic is of a transparent form. This facilitates cleaning. The device is also relatively unobtrusive when it is being worn. With the transparent form of the plastic, damage can be quickly detected.

The pads 5 of the present device are positioned between the posterior teeth Z of each side. On the side on which the patient bites more strongly, the fluid F is displaced from the pad 5 and forced via the tube 7 into the pad 5 on the opposite side. As a consequence, the posterior teeth Z on the other side are forced apart by the hydrostatic pressure building up in the pad 5. As a result, the temporomandibular joints and muscles are subjected to uniform loading on both sides when the device is being worn and one-sided loading is avoided. Dysfunctions of the temporomandibular joint caused as a result of one-sided loading can be treated with therapy in a simple, gentle, and nonobtrusive way.

An advantage of the device of the present invention is that the device is scarcely visible when it is being worn. For this purpose, parts of the device can be produced from a transparent plastic. Because of the clamping shoes 1 provided according to the invention, secure retention of the device is ensured. It can be worn unobtrusively and is scarcely any trouble or embarassment.

A number of embodiments of the invention have been described. Nevertheless, it will be understood that various modifications may be made without departing from the spirit and scope of the invention. Other embodiments are within the scope of the following claims.

What is claimed is:

1. A device for treating a temporomandibular joint, consisting essentially of:
   first and second pads (5), wherein said first and second pads comprise a cavity, wherein said cavity is filled with fluid (F), wherein said first and second pads (5) are in fluid communication with each other by means of a tube (7), wherein said first and second pads (5) comprise means (1, 3, 4, 8) for clamping said pads (5) on a posterior tooth (Z).

2. The device of claim 1, wherein said first and second pads are formed by an envelope produced from a flexible material.

3. The device of claim 1, wherein said means for clamping comprise at least one clip (8) bent in a way that corresponds to the contour of the posterior tooth (Z).

4. The device of claim 1, wherein said means for clamping comprise at least two clips (8) bent in a way that corresponds to the contour of the posterior tooth (Z).

5. The device of claim 3 or 4, wherein the clip (8) is cast into a clamping shoe (1), wherein said clamping shoe (1) is produced from plastic.

6. The device of claim 5, wherein the clamping shoe (1) is formed in a U profile with one or more legs (3, 4) extending from a base area (2).

7. The device of claim 6, wherein the height (H) of said one or more legs (3, 4) corresponds to the height of the posterior teeth (Z).

8. The device of claim 6, wherein said one or more legs (3, 4) comprise a buccal leg (3) and/or a lingual leg (4).

9. The device of claim 8, wherein said tube (7) is fastened to said buccal leg (3) of said clamping shoe (1).

10. The device of claim 8, wherein said tube (7) is connected to a passage (6) extending through said buccal leg (3) to said pad (5).

11. The device of claim 10, wherein the connection of said tube (7) to said passage (6) is located at one end (E) of said buccal leg (3).

12. The device of claim 5, wherein said clamping shoe (1) is produced in an integral form with at least one of said pads (5).

13. The device of claim 5, wherein said clamping shoe (1) is produced by thermoforming or by injection-molding.

14. The device of claim 5, wherein said plastic is transparent.

15. The device of claim 1, wherein said first and second pads are positioned on the occlusal surfaces of the posterior teeth (Z) of the left-hand and right-hand sides of a mouth.

* * * * *